United States Patent
Calderon

(10) Patent No.: US 8,945,630 B2
(45) Date of Patent: Feb. 3, 2015

(54) METHOD OF PRODUCING AND APPLICATIONS OF COMPOSITION OF HYPOCHLOROUS ACID

(75) Inventor: Justo Leonardo Calderon, Bogotáa (CO)

(73) Assignee: Aquilabs S.A., Bogota, D.C. (CO)

( * ) Notice: Subject to any disclaimer, the term of this patent is extended or adjusted under 35 U.S.C. 154(b) by 931 days.

(21) Appl. No.: 12/101,775

(22) Filed: Apr. 11, 2008

(65) Prior Publication Data

US 2009/0258083 A1    Oct. 15, 2009

(51) Int. Cl.
| | | |
|---|---|---|
| A01N 59/00 | (2006.01) |
| A61K 33/00 | (2006.01) |
| A01P 1/00 | (2006.01) |
| A01N 59/08 | (2006.01) |
| A61L 2/18 | (2006.01) |
| C01B 11/04 | (2006.01) |

(52) U.S. Cl.
CPC ............... *C01B 11/04* (2013.01); *A61K 33/00* (2013.01)
USPC . 424/600; 424/661; 252/187.25; 252/187.24; 252/187.26; 252/187.32

(58) Field of Classification Search
USPC ............... 424/600, 661; 252/187.25, 187.24, 252/187.26, 187.32
See application file for complete search history.

(56) References Cited

U.S. PATENT DOCUMENTS

| 4,190,638 A | * | 2/1980 | Hoekje et al. | ............... 423/473 |
| 4,971,999 A | * | 11/1990 | Bruckner et al. | ............ 514/698 |
| 2010/0285150 A1 | * | 11/2010 | Noguchi | ................. 424/661 |

FOREIGN PATENT DOCUMENTS

WO    WO 00/51434    * 9/2000 ............. A01N 59/08

OTHER PUBLICATIONS

Mellor: A comprehensive treatise on inorganic and theoretical chemistry, vol. II, Longmans, Green and Co., London, 1922.*
Wang, et al., Hypochlorous acid as a potential wound care agent, Part I. Stabilized hypochlorous acid: a component of the inorganic armamentarium of innate immunity, Journal of Burns and Wounds, 2007, vol. 6, p. 65-79.*

* cited by examiner

*Primary Examiner* — Ernst V Arnold
*Assistant Examiner* — Hong Yu
(74) *Attorney, Agent, or Firm* — Husch Blackwell, LLP

(57) ABSTRACT

A method for preparing a stabilized antimicrobial hypochlorous acid solution by diluting an aged stock solution to provide a hypochlorous acid solution at a concentration of about 50 to about 7000 ppm at a pH range of about 2.8 to about 4.0. The antimicrobial hypochlorous acid solution maintains at least 75 percent of the available chlorine present over a period of about 6 months to about 12 months. The antimicrobial hypochlorous acid solution has medical applications in humans and veterinary practice, both prophylactic and therapeutic. The solution can also be used for non-medical applications in antisepsis and sterilization of surfaces.

2 Claims, No Drawings

METHOD OF PRODUCING AND APPLICATIONS OF COMPOSITION OF HYPOCHLOROUS ACID

TECHNICAL FIELD

This invention contemplates a method of producing a stabilized composition of an antimicrobial hypochlorous acid solution and its applications for medical treatment and therapy, prophylactic treatment and non-medical treatment of waste and food products.

BACKGROUND OF THE INVENTION

After 1915, and as a result of the Great War, more than 200 bacterial action compounds were studied, among them hypochlorous acid. Hypochlorous acid was initially detected as an oxidizing agent generated by neutrophils. It was obtained from seawater.

Studies by Dakin in 1917 are reported using sodium hypochlorite diluted to 0.50% as an irrigation liquid for the cleaning and disinfection of contaminated wounds.

Later, in 1958, Agnes investigated hypochlorous acid as an immunological substance and defense mechanisms for granulocytes.

In 1989 Stephan J. Weiss in the *New England Journal of Medicine* conducted bacterial sensitivity studies on *E. coli* and toxicity on tissue in guinea-pigs.

There are currently several patents related to the production of hypochlorous acid, as mentioned below:

U.S. Pat. No. 4,190,638 entitled "Production of hypochlorous acid", owned by PPG Industries Inc., of Feb. 26, 1980 discloses that aqueous acid is produced by precipitating the acid through carbonation in a electrolytic cell where the cathode is liquid which is placed in contact with a bed fluidized with a mixture of gaseous chlorine and water vapor where the gas which is formed from the hypochlorous bed is absorbed by the water.

U.S. Pat. No. 4,908,215 entitled "Hypochlorite compositions containing thiosulphate and their use" of Mar. 13, 1990, discloses a process for disinfection, sterilization, bleaching and cleaning of a liquid or a surface comprised of: (a) producing an aqueous solution of hypochlorite, thiosulphate of earthy alkaline metal and a prebuffer in which the hypochlorite has an initial concentration of about 5 to 5000 ppm of chlorine and a molar ratio of thiosulphate to hypochlorite between 0.25:1 and 0.75:1; (b) adjusting the initial pH of the solution between 9.0 and 11.0 in contact with the surface or the liquid with the solution until the hypochlorite is consumed and the pH of the prebuffer solution decreases while the hypochlorite is consumed by the thiosulphate at the same time as the hypochlorite begins to depend on the initial pH of the solution.

U.S. Pat. No. 5,027,627 entitled "Production of Hypochlorous Acid" published on Aug. 6, 1991, discloses that hypochlorous acid is obtained by reaction of an aqueous solution of an alkaline metal hydroxide, forming drops with the gaseous chlorine to produce hypochlorous acid in vapor and particles of solid alkaline metal; a process where the molar ratio of the gaseous chlorine to the alkaline metal hydroxide is kept at least 22:1. The process includes the formation of impure chlorate in chlorinated alkaline metal particles. The hypochlorous acid produced contains 35-60% of weight dissolved in concentrated chlorine of at least about 2% by weight and is substantially free of ions of the alkaline metal and chlorine.

U.S. Pat. No. 5,322,677 entitled "Process for the production of a concentrated solution of hypochlorous acid", owned by Oil Corporation, published on Jun. 21, 1994, discloses a process for obtaining an aqueous hypochloric acid solution having an HOCl concentration of 50-60% by weight, which comprises making a aqueous solution of an alkaline metal hydroxide with 50% by weight with excess of chlorine gas react, reacting at 80-120 deg. C. to produce a mixture of monoxide, chlorine, hypochlorous acid vapor and water vapor, solid particles of chlorate alkaline metal of at least 10%.

WO 9514636 entitled "Manufacture of Hypochlorous Acid" owned by Joseph Repman, The Dow Chemical Company Trent and David, L., published Jun. 1, 1995, discloses a process which consists of contacting drops of an aqueous solution of hypochlorite metal having a volume median diameter of 500 mm with chlorine gas to produce hypochlorous acid. At least 80% of the hypochlorous acid produced in the preceding stage is vaporized to provide a vapor phase containing chlorine, water vapor, hypochlorous acid and dichlorine monoxide, leaving a liquid aqueous phase containing hypochlorous acid. The liquid phase hypochlorous acid solution is then distilled using a stripping gas containing at least 20 mole percent chlorine to separate gaseous hypochlorous acid and dichlorine monoxide from the aqueous brine.

U.S. Pat. No. 7,323,118, and the related European patent, EP 1432427, both entitled "Composition of hypochlorous acid and its applications", Calderon, co-assigned to Aquilabs S.A., disclose a composition of hypochlorous acid with medical applications in humans and in veterinary practice, both prophylactic and therapeutic. The composition of hypochlorous acid has 17 g/l of available chlorine, a pH value of 5-6, a density of 0.9-1.05 g/ml and an oxidation reduction potential of 1250-1450 m.v. The composition of hypochlorous acid is stated to have therapeutic use in a variety of medical applications.

U.S. Pat. No. 7,276,255 entitled "Wound and ulcer treatment with super-oxidized water", owned by Sterilox Medical (Europe) Limited, discloses a method for treating an open wound comprising administration of a hypochlorous acid solution having a pH value of 4 to 7, a redox potential of >950 mV, and being obtained by electrochemical treatment of a saline solution.

U.S. Pat. No. 6,426,066 entitled "Use of physiologically balanced, ionized, acidic solution in wound healing", owned by California Pacific Labs, Inc., filed on Jan. 12, 2000, discloses a solution prepared by the electrolysis of a solution comprising a mixture of inorganic salts in physiologically balanced proportions and the use of the physiologically balanced, acidic composition to treat wounds. The disclosed starting solution comprises salts ranging from about 0.4 g/L to about 16 g/L. The electrolyzed solution has a pH value within the range of about 2 to about 6, an oxidation reduction potential within the range of about 600 mV to about 1200 mV and titratable halide content within the range of about 10 ppm to about 100 ppm.

A family of patent applications related to U.S. Pat. No. 6,426,066 [U.S. application Ser. No. 10/000,919, Ser. No. 10/117,667, Ser. No. 10/209,681, Ser. No. 10/655,493 and PCT/US03/19126] disclose variations of the starting solution salt range, pH range, oxidation reduction potential and titratable halide content. The hypochlorous acid solution so prepared is also disclosed to be stable when stored in a chemically non-reactive container at room temperature over at least three months.

Wang et al., "Hypochlorous Acid as a Potential Wound Care Agent: Part I. Stabilized Hypochlorous Acid: A Component of the Inorganic Armamentarium of Innate Immunity", *Journal of Burns and Wounds,* 2007, Vol. 6:65-79, and Robson et al., "Hypochlorous Acid as a Potential Wound Care Agent: Part II. Stabilized Hypochlorous Acid: Its Role in Decreasing Tissue Bacterial Bioburden and Overcoming the Inhibition of Infection on Wound Healing", *Journal of Burns and Wounds,* 2007, Vol. 6:80-90, disclose the use of a stabilized hypochlorous acid solution prepared by acidifying reagent-grade NaOCl to a pH range of 3.5 to 4.0 with dilute HCl.

None of the above disclosures is believed to teach or suggest an antimicrobial hypochlorous acid solution that has the stability characteristics of those contemplated herein. The disclosure that follows illustrates the preparation of a contemplated stable solution.

BRIEF SUMMARY OF THE INVENTION

The present invention contemplates a process for producing an antimicrobial hypochlorous acid solution from dilution of an aged stock solution and the use of the antimicrobial hypochlorous acid solution in a variety of applications to treat infection and microbe contamination.

A contemplated antimicrobial hypochlorous acid solution is prepared as follows. An aqueous stock solution that contains an admixture of about 18 percent to about 22 percent solution A, about 1.0 percent to about 1.4 percent solution B, and about 70 percent to about 86 percent solution C is provided. Solution A contains about 13% sodium hypochlorite, solution B contains about 33 percent hydrochloric acid, and solution C is water, preferably deionized and/or distilled. Solution C and solution A are admixed to yield solution E that contains about 2 to about 3 percent sodium hypochlorite. The aqueous stock solution is formed by admixing solution E with solution B, thereby providing an aqueous stock solution that contains about 0.3 percent to about 0.5 percent hydrogen chloride. The aqueous stock solution has (i) a pH value of about 4 to about 6, and (ii) an oxidation reduction potential of about 850 m.v. to about 1450 m.v. The aqueous stock solution is maintained at ambient temperature in a sealed container in the substantial absence of light (in the dark) for about 18 to about 30 hours to form an aged stock solution. The antimicrobial hypochlorous acid solution is formed by i) diluting the aged stock solution to provide a hypochlorous acid solution at a concentration of about 50 to about 7000 ppm and ii) adjusting the pH value to about 2.8 to about 4.0, if needed. The antimicrobial hypochlorous acid solution, when sealed and in the substantial absence of light (in the dark) at a temperature of about 18 to about 20° C., maintains at least about 75 percent of the available chlorine present over a period of about 6 months to about 12 months. Available chlorine present is first measured at a time within about 24 hours after formation of the antimicrobial hypochlorous acid solution.

In optional, but preferred practice, solution E is admixed with solution D to form a salified (sodium chloride-containing) solution E. Solution D contains 0.006 percent to about 0.008 percent sodium chloride. A salified aqueous stock solution is formed by admixing the salified solution E with solution B. Here, the salified aqueous stock solution has (i) a pH value of about 4 to about 6, (ii) a conductivity of about 22 ds/m to about 27 ds/m., and (iii) an oxidation reduction potential of about 850 m.v. to about 1450 m.v. The salified aqueous stock solution is maintained at ambient temperature in a sealed container in the substantial absence of light (in the dark) for about 18 to about 30 hours to form an aged salified stock solution. The salified antimicrobial hypochlorous acid solution is formed by i) diluting the salified aged stock solution to provide a salified hypochlorous acid solution at a concentration of about 50 to about 7000 ppm and ii) adjusting the pH value to about 2.8 to about 4.0, if needed. The salified antimicrobial hypochlorous acid solution, when sealed and in the substantial absence of light (in the dark) at a temperature of about 18 to about 22° C., maintains at least about 75 percent of the available chlorine present over a period of about 6 months to about 12 months. Available chlorine present is first measured at a time within about 24 hours after formation of the salified antimicrobial hypochlorous acid solution.

The present invention has several benefits and advantages.

Salient among these benefits and advantages is the provision of an aqueous hypochlorous acid solution that is stable to degradation of its available chlorine concentration for six to about twelve months when stored in the substantial absence of light at a temperature of about 18 to about 22° C. Compositions containing similar amounts of the same ingredients when prepared by alternate methods do not achieve the exhibited stability of the present invention.

An advantage of the invention is that its method is easy to perform and follow, permitting workers possessing modest laboratory skills to prepare and use a contemplated solution.

In another benefit, a contemplated antimicrobial hypochlorous acid solution is not toxic, does not attack the skin and is fully biodegradable.

In another advantage, applications of antimicrobial hypochlorous acid solution for disinfection purposes result in rapid disinfection, occurring in seconds given the broader disinfection spectrum of hypochlorous acid. When used as a deodorant, the present invention destroys organic particles since it attacks mercaptan, methane and hydrosulphuric gases. Additionally the present invention has bacteriostatic powers for up to 24 hours.

Still further benefits and advantages will be apparent to a worker of ordinary skill from the discussion that follows.

In the context of the present invention and the associated claims, the articles "a" and "an" are used herein to refer to one or to more than one (i.e., to at least one) of the grammatical object of the article. By way of example, "an element" means one element or more than one element.

DETAILED DESCRIPTION OF THE INVENTION

The need that exists to find substances that do not cause reactions in an organism being treated and are highly effective in combating microorganisms resistant to antimicrobial agents and drugs has led to the study of hypochlorous acid, a substance that has the characteristics of minimizing morbidity and mortality produced by bacterial infections in comparison with normal saline solutions, a substance mostly used for washing the abdominal cavity and tissues.

Hypochlorous acid (HOCl) is a bactericide oxidant known particularly as an aqueous solution that attacks microorganisms dependent on $O_2$ in the place where they are produced. In particular, HOCl acts to modify various high-density proteins (as well as amino acids, lipids) that are first found in the plasma or the proteins of the plasmatic membrane, inhibiting synthesis.

Hypochlorous acid is an unstable compound that is highly reactive and known to be the strongest of the hypo halogenated acids and one of the most powerful oxidizing agents among chlorate oxacids. It is a weak acid with a dissociation constant of $2.9 \times 10^{-8}$ at 25° C. HOCl is stable in cold, diluted and pure solutions. The acid reacts with peroxide and gives off oxygen.

Protein can be highly toxic to cells and the biological function of HOCl is to deactivate or inhibit several systems of the endoplasmatic reticulum carrier (transport of glucose, several transporters of amino acids, proteins and Na+/K-ATPase) and generally cause harm to small molecules, making the cell inflate, subsequently causing cell death.

Hypochlorous acid can cause the death of highly resistant bacterial spores, several types of virus, macrobacteria with serous capsule (TB), and other vegetative bacteria and fungi in a concentration of 0.2% compared to other high-level microbiocide substances such as alkaline glutaraldehyde at 2% or hydrogen peroxide. HOCl can damage isolated DNA, cell death precedes oxidation of DNA in whole cells, in conjunction with myeloperoxide inhibits induced hydrogen peroxide ($H_2O_2$) and breaks down the DNA structure.

HOCl can also chlorinate bacterial nucleotides, disrupt membrane proteins, oxidize sulfhydryl groups of bacteria, cause fasting in bacteria and subsequent loss of bacterial capacity to restore energy, increase epithelial permeability, oxidize methionine and transform cystein into cysteic acid via inactivation of GroEl (a chaperone in *E. Coli*), limit proteolysis of the extracellular matrix via inhibition of the mmp-7 (metalloproteinase) through oxidation of methionine and the catalytic domain tryptophanglycine. HOCl is also involved in many other mechanisms known to one of ordinary skill in the art.

Chlorine concentrations of 0.25 are effective bactericides for many microorganisms except microbacteria, which are 500 times more resistant. Organic material in great part reduces antimicrobial activity of chlorine. Hypochlorous acid is also a bactericide agent which attacks microorganisms at the place where they proliferate, prepared in the immune system by nuclear polymorph neutrophils that migrate and adhere to the endothelial cells to act as a mediator in inflammation, increasing the permeability of the vascular endothelium for cellular participation and to kill antigens.

HOCl is produced by hydrogen peroxide ($H_2O_2$), a chlorine ion, in reaction with the enzyme myeloperoxidase. Myeloperoxidase converts $H_2O_2$ into a reasonable microbiocidal agent and HOCl into an excellent microbiocide. Myeloperoxidase diverts the genotoxic $H_2O_2$ into HOCl, which is highly toxic for the tissue in a free protein system, but is considerably less toxic in vivo.

Hypochlorous acid protects against a variety of organisms including, but not limited to, gram negative bacteria, gram positive bacteria, anaerobic bacteria, virus and fungus (such as *Escherichia coli*, Pulmonary *Klebsiella*, *Proteus*, *Pseudomonas*, *Staphylococcus aureus*, *Hemolitic Streptoccocus*, *Enterococcus*, *Salmonella*, *Clostridium*, HIV, *Coagulaze staphylococcus* (−Y+), *Enterobacter aerogenes*, *Aspergillus flavus*, and *Bacillus* SPP).

The process of preparing an antimicrobial hypochlorous acid solution of the present invention comprises a chemical reaction of chlorinated elements in natural solvent at boiling point through reaction in a pressurized reactor. The antimicrobial hypochlorous acid solution is formed from a stock solution of hypochlorous acid with a content of about 17 g/l of available chlorine.

In preparing an antimicrobial hypochlorous acid solution, a solution of about 13 percent sodium hypochlorite is added to aqueous solvent to obtain a concentration of sodium hypochlorite of about 2.6 percent and shaking the mixture for about 3 minutes, optionally and preferably followed by the addition of an about 1.0 percent sodium chloride solution to achieve a concentration of sodium chloride of about 0.4125 percent and shaking the mixture for about 15 seconds, followed by the addition of an about 33 percent solution of hydrochloric acid to achieve a concentration of hydrochloric acid of about 0.0075 percent and generate a reaction in the solution for formation of a stock solution to use in the preparation of an antimicrobial hypochlorous acid solution.

The process of preparing a stock solution for preparation of an antimicrobial hypochlorous acid solution is outlined in the protocol below:
Solution A: Primary Base in Chlorinated Salt (i.e. 13% NaOCL)
Solution B: Chlorinated reactive (i.e. 33% HCl)
Solution C: Distilled and/or Deionized Water
Solution D: halide—comprising salt (i.e. NaCl)

For preparation of a stock solution, fill a container with about 70 percent to about 86 percent, preferably 78 percent, total volume solution C; followed by subsequent addition of about 18 percent to about 22 percent, preferably 20 percent total volume solution A and shake for about 3 minutes; followed by the addition of about 0.6 percent to about 0.8 percent total volume, preferably 0.75 percent total volume of solution D and shake for 15 seconds; finally adding about 1.0 percent to about 1.4 percent, preferably 1.25 percent total volume solution B to generate a reaction in the solution and form said stock solution.

In an alternate embodiment, solution D is optional in the preparation of stock solution and ultimately, an antimicrobial hypochlorous acid solution can be prepared with solutions A, B, and C.

For preparation of an antimicrobial hypochlorous acid solution or salified antimicrobial hypochlorous acid solution, the stock solution is diluted to the desired concentration and utilized for the desired purpose.

The uses and properties herein apply equally to the an antimicrobial hypochlorous acid solution as they do to a salified antimicrobial hypochlorous acid solution.

The antimicrobial hypochlorous acid solution can be administered via topical administration onto surfaces such as countertops. Topical administration of the solution can also be used for treatment of wounded or burned regions of the skin, wherein the solution is placed on a piece of gauze prior to or subsequent to placing the gauze over the regions. The solution can also be administered parenterally for treatment of systemic infections.

In another aspect, an antimicrobial hypochlorous acid solution of the invention contains hypochlorite ions at a concentration of about 2.34 percent to about 2.86 percent, preferably about 2.6 percent, of the aqueous stock solution.

In another aspect, an antimicrobial hypochlorous acid solution of the invention contains hydrochloric acid at a concentration of about 0.33 percent to about 0.46 percent, preferably about 0.41 percent, of said aqueous stock solution.

In yet another aspect, an antimicrobial hypochlorous acid solution of the invention contains sodium chloride at a concentration of about 0.006 percent to about 0.008 percent, preferably about 0.0075 percent, of said aqueous stock solution.

In a further aspect, an antimicrobial hypochlorous acid solution exhibits conductivity of about 23 ds/m to about 26 ds/m, preferably about 24 ds/m to about 26 ds/m, and most preferably about 25.3 ds/m.

In a further aspect, an antimicrobial hypochlorous acid solution exhibits an oxidation reduction potential of about 850 m.v. to about 1450 m.v., preferably about 1100 m.v. to about 1450 m.v., and more preferably about 1250 m.v. to about 1450 m.v.

In an alternate aspect of the invention, an antimicrobial hypochlorous acid solution exhibits an oxidation reduction potential of at least 1000 m.v.

In another aspect of the invention, an antimicrobial hypochlorous acid solution exhibits stability wherein the antimicrobial hypochlorous acid solution maintains at least about 90 percent of the available chlorine present over a period of about 6 to 12 months.

In another aspect of the invention, an antimicrobial hypochlorous acid solution has a pH value of about 3.7 to about 4.0.

In another aspect of the invention, an antimicrobial hypochlorous acid solution contains about 3500 to about 7000 ppm hypochlorous acid. Here, the solution can be used for: i) cleansing pathogen-contaminated surfaces comprising contacting the surfaces with the antimicrobial hypochlorous acid solution, and ii) disabling pathogens in organic waste comprising contacting said waste with said solution, wherein said waste can be a member of the group consisting of: biohazardous waste, food production waste, landfill waste, bodily fluid waste, medical laboratory waste, medical treatment room waste, and medical surgical room waste.

In another aspect of the invention, the biohazardous waste treated with an antimicrobial hypochlorous acid solution can be generated from an emergency room, a clinical laboratory, a blood bank, a maternity room, a surgical room, a morgue, and a portable toilet room.

In another aspect of the invention, an antimicrobial hypochlorous acid solution contains about 460 to about 500 ppm hypochlorous acid. Here, the solution can be used for cleansing exposed bodily regions subject to surgical procedures whereby one or more such regions is contacted with the antimicrobial hypochlorous acid solution. A further use of this solution is for cleansing and treating bodily regions subject to injury from orthopedic procedures.

In a further aspect of the invention, an antimicrobial hypochlorous acid solution contains about 380 to about 530 ppm hypochlorous acid. Here, the solution can be used for treating sites of respiratory tract infection in which the antimicrobial hypochlorous acid solution is delivered to those sites by nebulization of the solution the antimicrobial hypochlorous acid solution to said sites.

In yet another aspect of the invention, an antimicrobial hypochlorous acid solution contains about 460 ppm hypochlorous acid and can be used for treating burned epithelial tissues comprising contacting said tissues with the antimicrobial hypochlorous acid solution.

In another aspect of the invention, an antimicrobial hypochlorous acid solution contains about 50 to about 500 ppm hypochlorous acid is used for treating leishmaniasis-infected cutaneous tissues by contacting those infected cutaneous tissues with the antimicrobial hypochlorous acid solution.

In another aspect of the invention, an antimicrobial hypochlorous acid solution contains about 400 to about 430 ppm hypochlorous acid and is used for eliminating sites of systemic parasitic infection. Here, a site of systemic parasitic infection is contacted by parenteral administration of the antimicrobial hypochlorous acid solution.

In another aspect of the invention, an antimicrobial hypochlorous acid solution contains about 470 to about 550 ppm hypochlorous acid and is used for treating intragastric and systemic bacteria. In this embodiment, the bacteria are contacted with the antimicrobial hypochlorous acid solution.

In a further aspect of the invention, an antimicrobial hypochlorous acid solution contains about 1000 ppm hypochlorous acid and is used for disinfecting oral hygiene products and comprises contacting those products with the antimicrobial hypochlorous acid solution.

In an additional aspect of the invention, an antimicrobial hypochlorous acid solution contains about 500 ppm hypochlorous acid and is used for i) treating infection of the periodontal cavities and comprises contacting those cavities with the antimicrobial hypochlorous acid solution, or ii) irrigating a periodontal cavity irrigation bag comprising contacting interior of such a bag with the antimicrobial hypochlorous acid solution.

In another aspect of the invention, an antimicrobial hypochlorous acid solution contains about 1500 to about 3000 ppm hypochlorous acid and is used for disabling microbes residing on a surface and comprises contacting the surface with the antimicrobial hypochlorous acid solution.

In another aspect of the invention, an antimicrobial hypochlorous acid solution contains about 500 to about 600 ppm hypochlorous acid and is used for disinfecting hands comprising washing said hands with the antimicrobial hypochlorous acid solution.

In a further aspect of the invention, an antimicrobial hypochlorous acid solution contains about 700 to about 1000 ppm hypochlorous acid and is used for cleansing hands comprising preparing a hand soap containing the antimicrobial hypochlorous acid solution and washing the hands with that hand soap.

In another aspect of the invention, an antimicrobial hypochlorous acid solution contains about 460 to about 500 ppm hypochlorous acid and is used for i) cleansing facial skin or ii) treating acne. Both uses comprise contacting said skin with the antimicrobial hypochlorous acid solution.

In each of the above uses of a contemplated antimicrobial hypochlorous acid solution, the solution is maintained in contact with the contacted surface, tissues or cells for a time sufficient to kill at least 99 percent (substantially all) of the microbes present at the site of contact. Solutions that contain about 500 ppm hypochlorous acid or less can be left in contact with the surface or cells for substantially any length of time. That is, a solution can be applied and never removed. For an antimicrobial hypochlorous acid solution that contains more than about 500 ppm of hypochlorous acid, contact is maintained for a few seconds to a few minutes, and the solution is removed from the site of contact.

The stability of a contemplated antimicrobial hypochlorous acid solution refers to maintaining at least about 75% of the original concentration of available chlorine, and depends on a variety of factors including, but not limited to, chlorine concentration, pH of the solution, temperature of the solution and exposure to light. The solution should not be heated, as the resulting concentration of hypochlorite over time at elevated temperature will decrease. If the solution is maintained in a properly closed and sealed container as to not allow the escape of gas formed, the solution is more resistant to temperature changes. The solution is covered to prevent decomposition. Cooling the solution does not affect the composition and manufacturing should be carried out at room temperature. The solution should be protected from sunlight and moisture and stored at room temperature in a dark colored bottle or a vessel through which light cannot penetrate. Under these storage conditions, an antimicrobial hypochlorous acid solution of the present invention is stable for up to about 6 to about 12 months and in a preferred embodiment, up to about 24 months.

To determine the stability of the antimicrobial hypochlorous acid solution or salified antimicrobial hypochlorous acid solution of the present invention, a determination as to the amount of available chlorine as hypochlorous acid can be made by the titrimetric or iodometric test known to one of ordinary skill in the art. This test for available chlorine of the antimicrobial hypochlorous acid solution or salified antimicrobial hypochlorous acid solution prepared by the above methods should be carried out immediately following preparation of the antimicrobial hypochlorous acid solution or salified antimicrobial hypochlorous acid solution, wherein the term 'immediately' means within a time period of about 24 hours. It is this initial testing value that is to be compared to the later time point at 6, 12, or 24 months time to establish proper stability of at least 75 percent retention of the available chlorine in solution.

EXAMPLES

The present invention is described in the following examples which are set forth to aid in the understanding of the invention, and should not be construed to limit in any way the invention as defined in the claims which follow thereafter.

In each Example described below, the treatment regimen involved daily topical applications of an about 460 ppm antimicrobial hypochlorous acid solution at a pH between 3.7 and 4.7.

Example A

Treatment of Varicose Ulcers

A patient with varicose ulcers was treated over a course of 10 months an antimicrobial hypochlorous acid solution of the present invention. The patient exhibited substantial recovery from the ulcers after the ten month time course.

Example B

Treatment of Infections Resulting from Surgery

A patient presented with severe leg infection post surgery. At 12 days post treatment, the infection was substantially reduced and at 20 days post treatment the wound was substantially closed and exhibited minimal infection.

Example C

Treatment of Burns

A patient with a hand burned by hot wax presented with severe redness and scabbing prior to treatment, and 10 days after initiation of treatment the scabbing was gone and only minor redness remained in the burned areas.

Example D

Stability Testing

An antimicrobial hypochlorous acid solution of the present invention shows stability with retention of greater than 75 percent of the available chlorine measured by the titrimetric assay as illustrated in Table I. The stability study shown below was carried out by ProQuiFar, Ltda., Laboratorio de Control de Calidad, Bogota, Columbia.

Stability Study
[data shown as a % of 330 ppm hypochlorous acid identified by titrimetric method in antimicrobial hypochlorous acid solution]

| Solution | Zero Time | Time and Temperature Conditions for Solution ||| 3 months at room temperature |
| | | 1 month @ 41° C. | 2 months @ 41° C. | 3 months @ 41° C. | |
| --- | --- | --- | --- | --- | --- |
| A* | 132.3% | 123.2% | 108.1% | 96.97% | 130.3% |
| B* | 131.3% | 117.2% | 105.07% | 97.97% | 127.3% |

*denotes average of three separate trials

The foregoing description and the examples are intended as illustrative and are not to be taken as limiting. Still other variations within the spirit and scope of this invention are possible and will readily present themselves to those skilled in the art.

What is claimed is:

1. A method of preparing a stabilized composition of an antimicrobial hypochlorous acid solution comprising the steps of:
   a) providing an aqueous stock solution that contains an admixture of about 18 percent to about 22 percent solution A, about 1.0 percent to about 1.4 percent solution B, and about 70 percent to about 86 percent solution C, wherein said solution A contains about 13 percent sodium hypochlorite, said solution B contains about 33 percent hydrochloric acid, and said solution C is water,
   b) admixing said solution C and said solution A to yield solution E, wherein said solution E contains about 2 to about 3 percent sodium hypochlorite,
   c) forming said aqueous stock solution by admixing said solution E with said solution B, wherein said aqueous stock solution contains about 0.3 percent to about 0.5 percent hydrogen chloride,
   wherein said aqueous stock solution has (i) a pH value of about 4 to about 6, and (ii) an oxidation reduction potential of about 1100 m.v. to about 1450 m.v., said aqueous stock solution being maintained at ambient temperature in a sealed container in the dark for about 18 to about 30 hours to form an aged stock solution; and
   d) forming said antimicrobial hypochlorous acid solution by i) diluting said aged stock solution to provide a hypochlorous acid solution at a concentration of about 1500 to about 3000 ppm i) adjusting the pH value to about 2.8 to about 4.0, said antimicrobial hypochlorous acid solution, when sealed and in the dark (in the dark) at a temperature of about 18 to about 22° C., maintaining at least about 75 percent of the available chlorine present as hypochlorous acid over a period of about 6 months to about 12 months, wherein available chlorine present is first measured at a time within about 24 hours after formation of the antimicrobial hypochlorous acid solution.

2. The method of claim 1, further comprising the steps to form a salified antimicrobial hypochlorous acid solution:
   b') admixing said solution E with solution D to form a salified solution E, said solution D containing 0.006 percent to about 0.008 percent sodium chloride,
   b") forming salified aqueous stock solution by admixing the salified solution E with said solution B,
   wherein said salified aqueous stock solution has (i) a pH value of about 4 to about 6, (ii) a conductivity of about 22 ds/m to about 27 ds/m., and (iii) an oxidation reduction potential of about 1100 m.v. to about 1450 m.v., said aqueous stock solution being maintained at ambient temperature in a sealed container in the dark for about 18 to about 30 hours to form an aged salified stock solution; and d) forming said salified antimicrobial hypochlorous acid solution by i) diluting said salified aged stock solution to provide a salified hypochlorous acid solution at a concentration of about 1500 to about 3000 ppm and ii) adjusting the pH value to about 2.8 to about 4.0, said salified antimicrobial hypochlorous acid solution when sealed and in the dark at a temperature of about 18 to about 22° C. maintains at least about 75 percent of the available chlorine present over a period of about 6 months to about 12 months, wherein said available chlorine present as hypochlorous acid is first measured at a time after formation of said salified aged stock solution.

* * * * *